(12) United States Patent
Mattison (10) Patent No.: US 12,403,441 B2
(45) Date of Patent: Sep. 2, 2025

(54) COLLOIDAL BREWING SYSTEM

(71) Applicant: Gaile Mattison, Rochester, MN (US)

(72) Inventor: Gaile Mattison, Rochester, MN (US)

( * ) Notice: Subject to any disclaimer, the term of this patent is extended or adjusted under 35 U.S.C. 154(b) by 880 days.

(21) Appl. No.: 17/665,888

(22) Filed: Feb. 7, 2022

(65) Prior Publication Data

US 2022/0250023 A1 Aug. 11, 2022

Related U.S. Application Data

(60) Provisional application No. 63/147,230, filed on Feb. 8, 2021.

(51) Int. Cl.
| | | |
|---|---|---|
| *C25C 5/00* | (2006.01) | |
| *A01N 59/16* | (2006.01) | |
| *A61K 33/38* | (2006.01) | |
| *A61L 15/18* | (2006.01) | |
| *A61L 15/44* | (2006.01) | |
| *B01F 33/453* | (2022.01) | |
| *B01J 13/00* | (2006.01) | |
| *C25C 5/02* | (2006.01) | |

(52) U.S. Cl.
CPC .......... *B01J 13/0043* (2013.01); *A01N 59/16* (2013.01); *A61K 33/38* (2013.01); *A61L 15/18* (2013.01); *A61L 15/44* (2013.01); *B01F 33/4534* (2022.01); *C25C 5/02* (2013.01); *A61L 2300/104* (2013.01); *A61L 2300/404* (2013.01); *A61L 2400/12* (2013.01)

(58) Field of Classification Search
CPC .. B01J 13/0043; B01F 33/4534; A01N 59/16; A61L 15/18; A61L 15/44; C25C 5/02
See application file for complete search history.

(56) References Cited

U.S. PATENT DOCUMENTS

| | | | | |
|---|---|---|---|---|
| 2011/0068013 A1* | 3/2011 | Choi | ........................ | C25C 1/20 |
| | | | | 977/773 |
| 2015/0359380 A1* | 12/2015 | Oleksy | ................. | A47J 31/462 |
| | | | | 426/433 |
| 2016/0000088 A1* | 1/2016 | Nakamura | ............... | A61K 8/19 |
| | | | | 424/618 |
| 2016/0281249 A1* | 9/2016 | Salazar | ..................... | C25C 5/02 |
| 2020/0093315 A1* | 3/2020 | Burrows | ............... | A47J 31/461 |

* cited by examiner

*Primary Examiner* — Zulmariam Mendez
(74) *Attorney, Agent, or Firm* — Jose W. Jimenez; Robert Cantrell; Jimenez Law Firm (57) ABSTRACT

A colloidal brewing system has a transparent container assembly with a watertight bottom portion and an open top portion, the container assembly adapted to contain water. A removable lid electronic housing with two replaceable electrically charged silver rod members is disposed on a bottom portion of the lid member, the rod members extending substantially to near the bottom of the container assembly. A magnetic stir assembly substantially centers an interior bottom portion of the container assembly and to rotate, in the water, on a parallel plane to the bottom portion. A receiver and transmitter coil assembly are disposed within a base container assembly, the base container assembly designed to gravitationally support the watertight bottom portion of the transparent container assembly, the receiver coil and transmitter coil assembly inductively coupled to the magnetic stir assembly. The inventive concept has a rechargeable battery, a control panel, power port members, and handle member.

20 Claims, 9 Drawing Sheets

COLLOIDAL BREWING SYSTEM

CLAIM OF PRIORITY

This application claims priority to and the benefit of U.S. Provisional Application with Ser. No. 63/147,230, filed on Feb. 8, 2021, with the same title, the contents of which are hereby incorporated by reference in its entirety.

FIELD OF THE INVENTION

The inventive concept relates generally to a colloidal brewing system.

BACKGROUND

Colloidal silver products may be antimicrobial, germ-fighting, and immunity-boosting agents. One or more of silver nanoparticles and microparticles are incorporated into bandages and dressings for wounds and burn treatment. Colloidal silver may be used as a supplement to fight viruses. Colloidal silver may be consumed as a supplement, used topically, and put in a spray bottle as a house-cleaning product to eliminate germs, mold, and viruses or may be used as a spray to protect garden plants from fungi and insects.

Currently, people may attempt to brew colloidal silver on their own, but this solution is unable to meet the needs of the market because brewing colloidal silver can be difficult. Therefore, there currently exists a need in the market for an improved apparatus that brews colloidal silver.

SUMMARY OF THE INVENTION

A colloidal brewing system has a transparent container assembly with a watertight bottom portion of the container assembly and an open top portion of the container assembly, the container assembly designed to preferably contain distilled water. Water is typically substantially distilled water, but other aqueous solutions may be used. A removable lid member encases at least one positive and negative (removable/replaceable) electrical wire members therein with removable/replaceable two silver rod members being disposed seated or disposed on a bottom portion of the lid member, the rod members extending substantially to near the bottom portion of the container assembly. A magnetic stir assembly substantially centers an interior bottom portion of the container assembly and is designed to rotate on a parallel plane to the bottom portion of the container assembly. A receiver coil and a transmitter coil assembly are disposed within a base container assembly, the base container assembly designed to gravitationally support the watertight bottom portion of the transparent container assembly, the receiver coil and transmitter coil assembly inductively coupled to the magnetic stir assembly. A handle portion is coupled to an at least one side portion of the transparent container assembly. At least one positive and negative electrical wire members are disposed through an interior portion of the handle assembly designed to electrically couple the rod members to the receiver and transmitter coil assembly. A rechargeable battery assembly is disposed within the base container assembly electrically coupled to at least one power port member. A control panel is disposed in the base container assembly designed to control the power and timing of the magnetic stir assembly.

In one embodiment of the colloidal brewing system, the power port member is a micro-SB port assembly.

In one embodiment of the colloidal brewing system, the power port member is an AC/DC power adapter assembly.

In one embodiment of the colloidal brewing system, a spout portion is disposed on the at least one side portion opposite the handle portion.

It would be advantageous to have a colloidal brewing system that is reusable. Furthermore, it would be advantageous to have a colloidal brewing system that has a light emitting diode (LED) display. Still further, it would be advantageous to have a colloidal brewing system that is magnetic.

The inventive concept advantageously fills the aforementioned deficiencies by providing a colloidal brewing system, which provides an aesthetically appealing, cost-effective way to obtain colloidal silver.

The inventive concept is a home colloidal brewing system.

The colloidal brewing system has a magnetic stirring mechanism.

The colloidal brewing system fulfills the need for a colloidal silver brewing device.

Among other things, it is an advantage of the colloidal brewing system to provide a colloidal brewing system that does not suffer from the problems of exposed wires affixed to a jar or other deficiencies associated with prior solutions It is still further an advantage of the colloidal brewing system to be compact.

Still further, the colloidal brewing system may have a USB and AC/DC power adapter.

The inventive concept now will be described more fully hereinafter with reference to the accompanying drawings, which are intended to be read in conjunction with both this summary, the detailed description and any preferred and/or particular embodiments specifically discussed or otherwise disclosed. This inventive concept may, however, be embodied in many different forms and should not be construed as limited to the embodiments set forth herein; rather, these embodiments are provided by way of illustration only and so that this disclosure will be thorough, complete, and will fully convey the full scope of the inventive concept to those skilled in the art.

DETAILED DESCRIPTION OF THE INVENTION

Following are more detailed descriptions of various related concepts related to, and embodiments of, methods and apparatus according to the present disclosure. It should be appreciated that various aspects of the subject matter introduced above and discussed in greater detail below may be implemented in any of numerous ways, as the subject matter is not limited to any particular manner of implementation. Examples of specific implementations and applications are provided primarily for illustrative purposes.

Referring to the figures, FIGS. 1-9 illustrate a colloidal brewing system 100 having a transparent or translucent container assembly 110 with a watertight bottom portion 119 and an open top portion 111, container assembly 110 designed to contain distilled water, water-based or an aqueous solution 110. A removable lid member 120 that includes, encases seats at least one positive and negative electrical wire members 122A and 122B therein. In this example embodiment, wire members 122A and 122B are coupled to two removable silver rod members 47A and 47B suspended in the transparent container assembly 110 filled with distilled water 110. The silver rod members 47A and 47B are disposed on and coupled to a bottom portion 129 of the lid member 120, with the rod members 47A-47B extending substantially to near the bottom portion 119 of the container assembly 110. In other embodiments, silver rod members 47, or other beneficial metals or mineral rods, can be of varying and shorter lengths but are necessary to be substantially submerged in distilled water during brewing.

Figure 1:
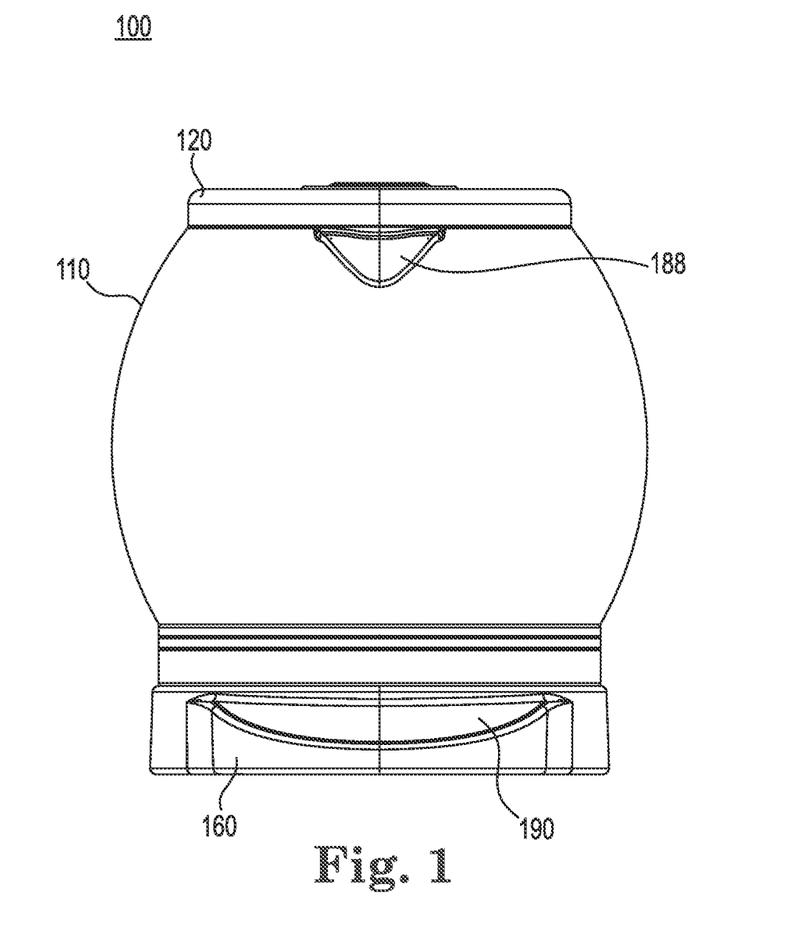
FIG. 1 illustrates the front of the colloidal brewing system.
Figure 2:
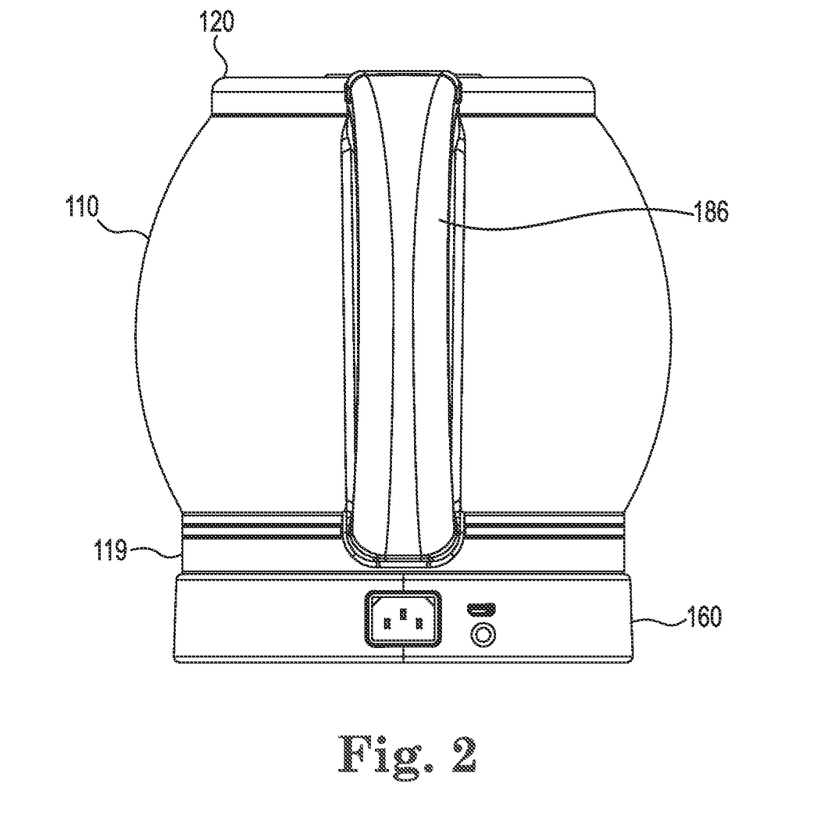
FIG. 2 illustrates the back of the colloidal brewing system.
Figure 3:
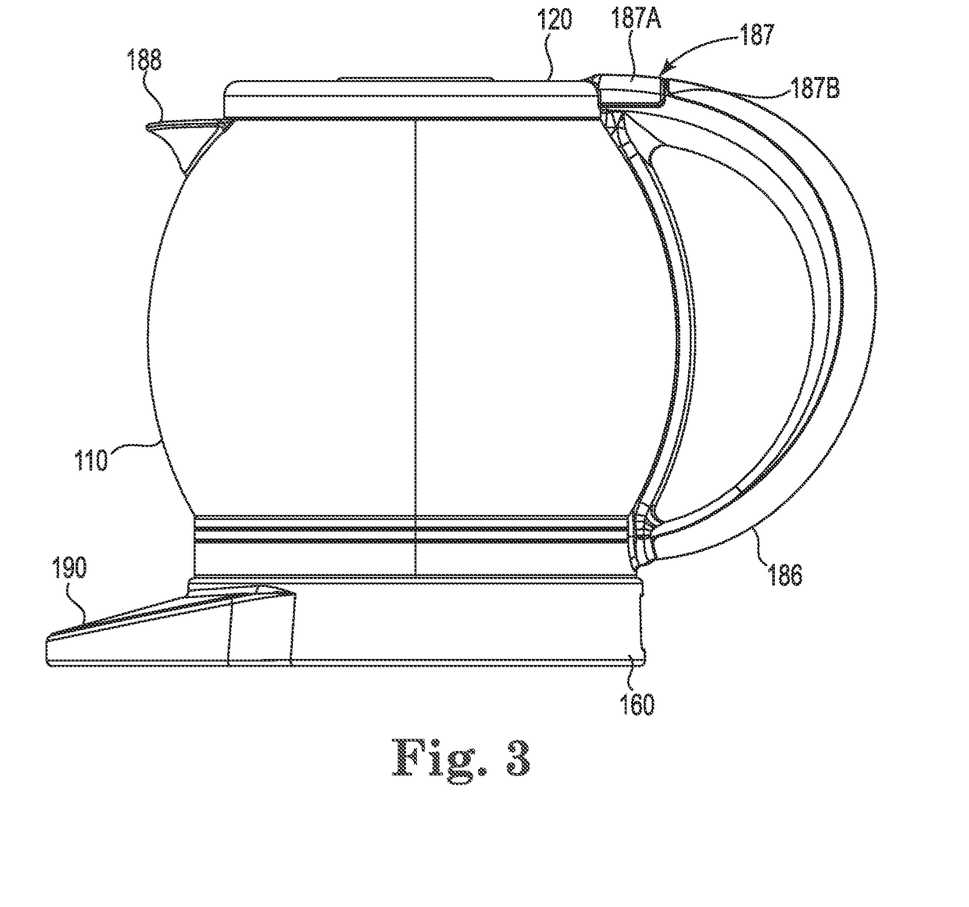
FIG. 3 illustrates the right side of the colloidal brewing system.
Figure 4:
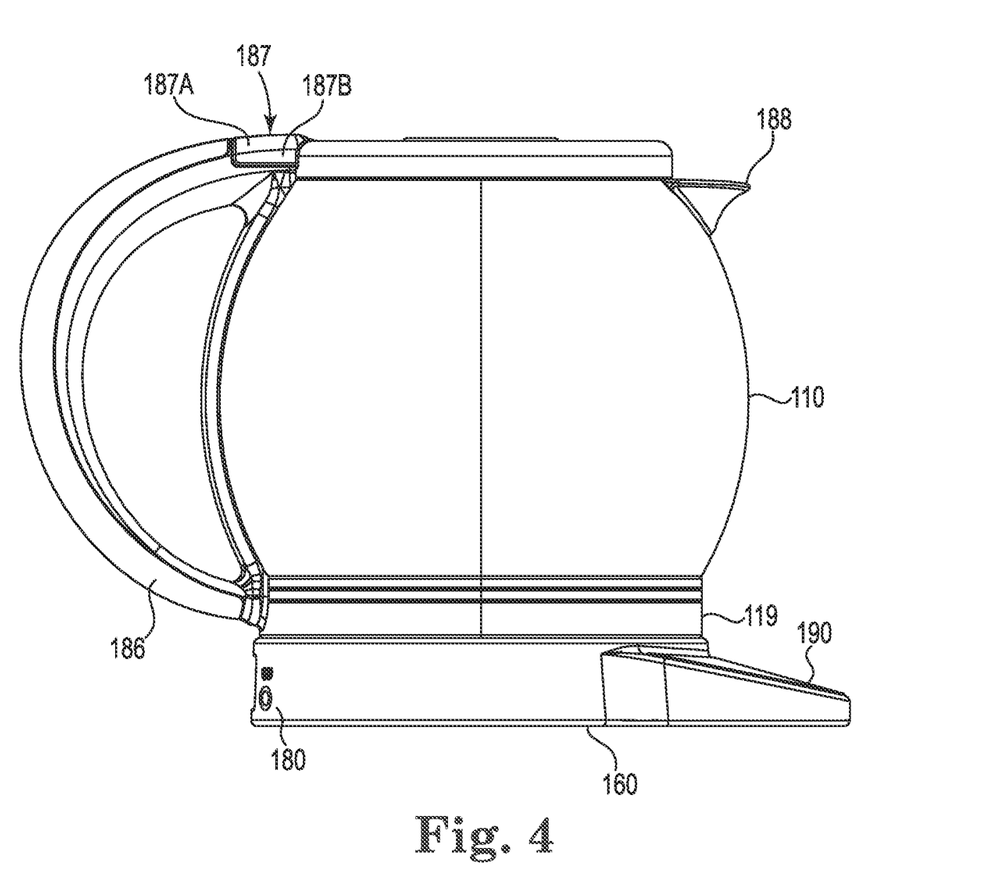
FIG. 4 illustrates the left side of the colloidal brewing system.
Figure 5:
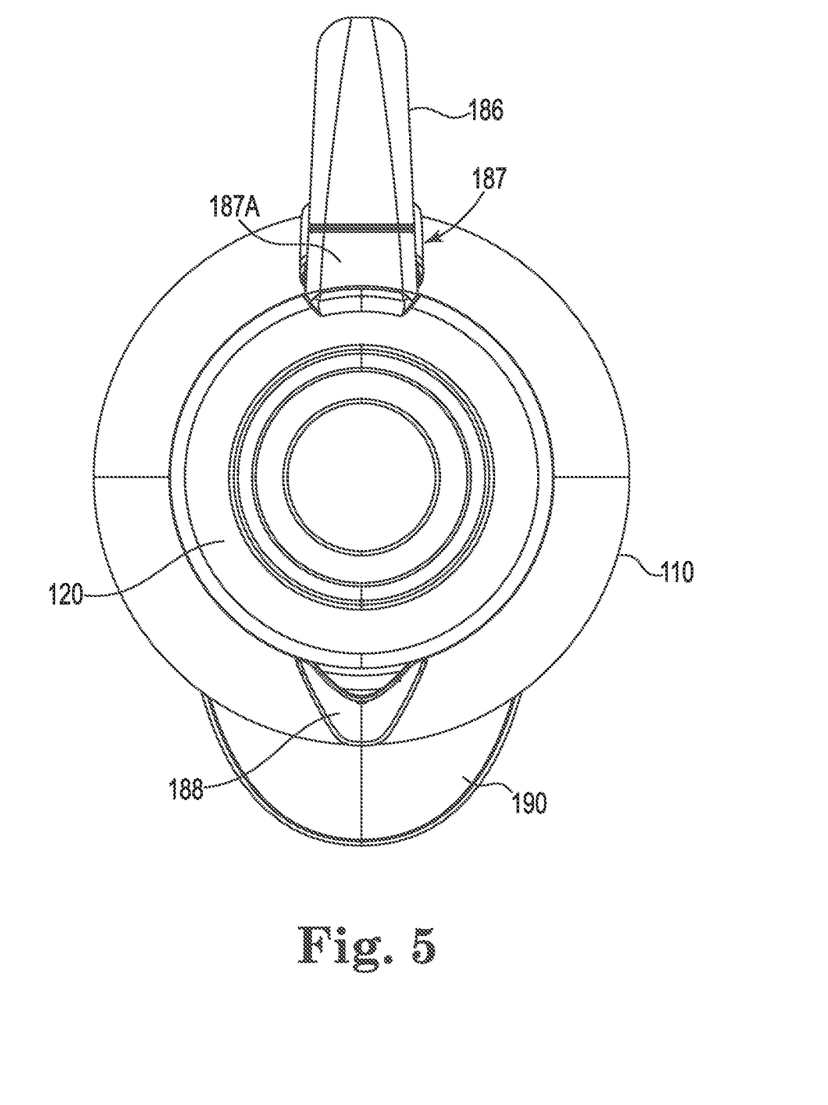
FIG. 5 illustrates the top of the colloidal brewing system.
Figure 6:
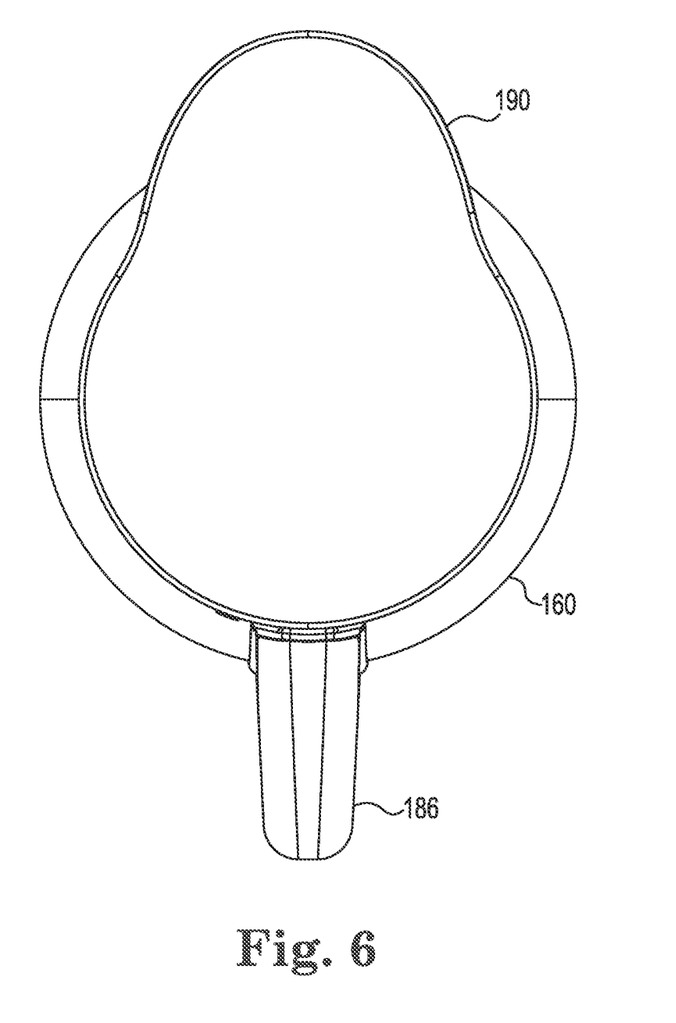
FIG. 6 illustrates the bottom of the colloidal brewing system.
Figure 7:
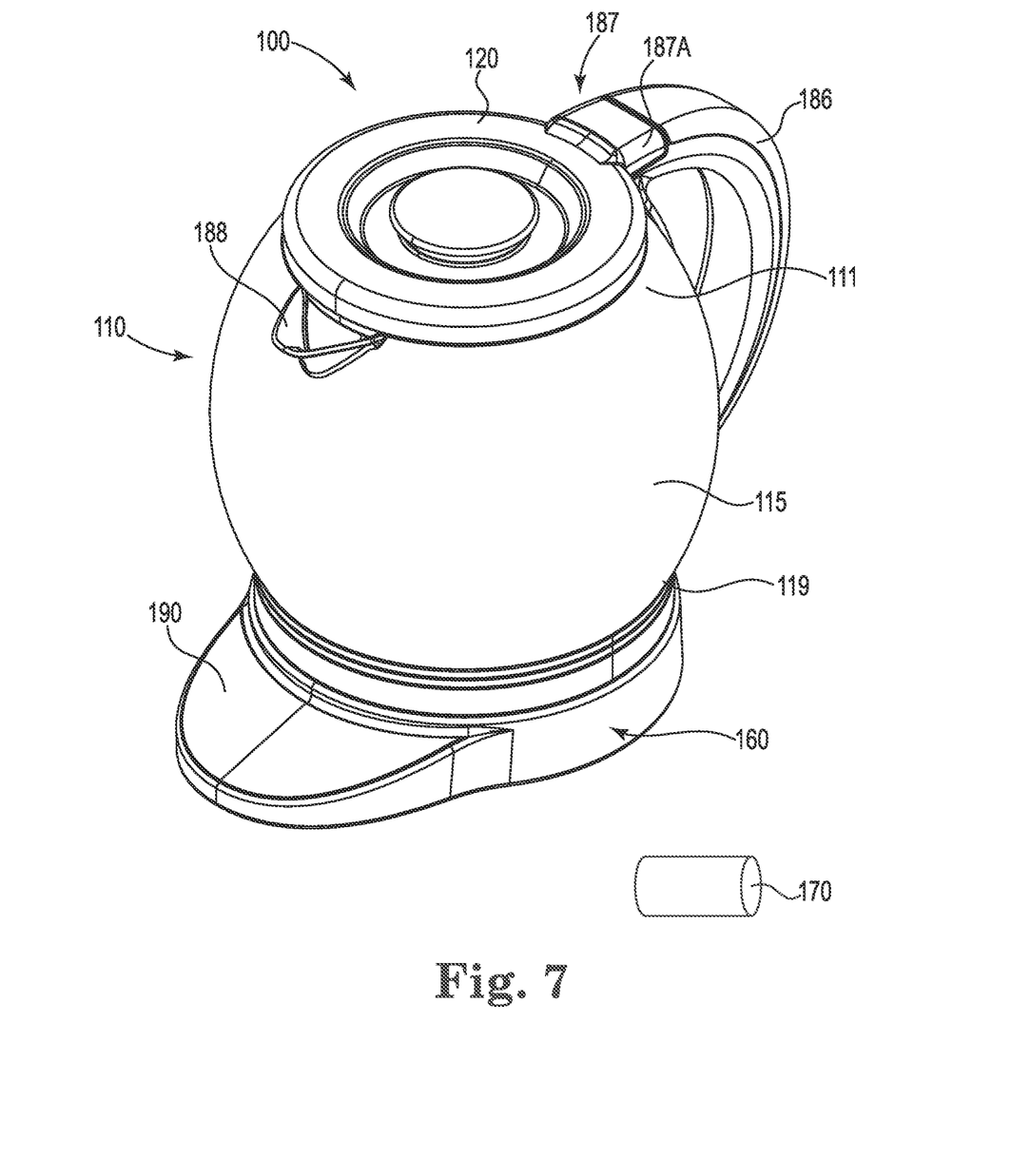
FIG. 7 illustrates the perspective view of the colloidal brewing system.
Figure 8:
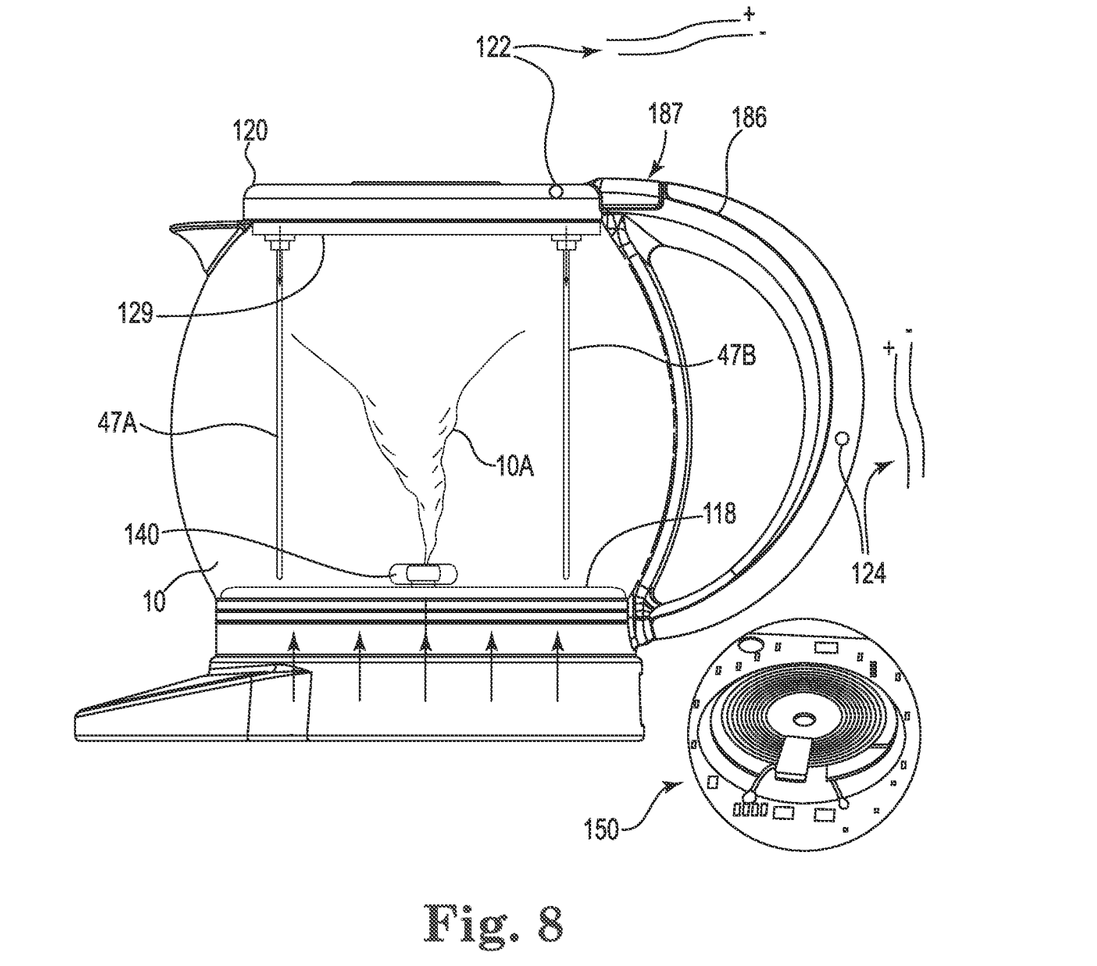
FIG. 8 illustrates the interior view of the colloidal brewing system.
Figure 9:
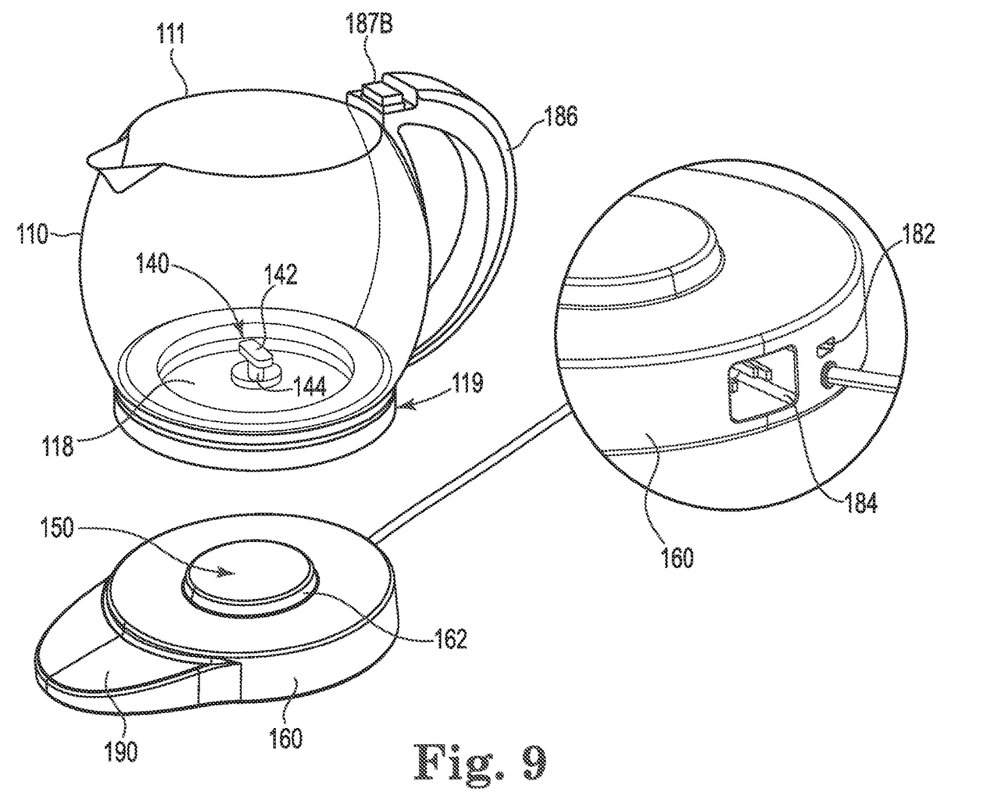
FIG. 9 illustrates a semi-exploded view of the colloidal brewing system separating the transparent container from the base.

In this embodiment, system 100 includes a magnetic stir assembly 140 which substantially centers an interior bottom portion 118 of the container assembly 110 and is designed to rotate on a parallel plane 119 to the bottom portion 118. Assembly 140 includes an impeller 142 coupled to a stem or rod 144 to facilitate spinning when a magnetic inductive force is applied. In a related embodiment, impeller 142 and rod 144 can be substituted with a magnetic capsule designed for spinning when an inductive magnetic force is applied. Referring briefly to FIG. 8, assembly 140 ensures that clumping of the silver particles in water 10 solution is eliminated or kept to a minimum (see swirling water 10A caused by spinning impeller 142), and the silver particles are mixed well in the distilled water 10, in order that the final colloidal silver (or other metal or mineral, such as zinc) solution or "brew" has a defined brew time in hours and minutes (of about an hour or so depending on the level of silver particles desired in the water) or a level of silver particles, preferably 5-12 parts per million (ppm).

In this example embodiment, a receiver coil and a transmitter coil assembly 150 are disposed within a base container assembly 160, the base container assembly 160 being designed to gravitationally support the watertight bottom portion 119 of the transparent container assembly 110. Receiver coil 150A and transmitter coil 150B of assembly 150 is inductively coupled to the magnetic stir assembly 140. A handle portion 186 is coupled to an at least one side portion of the transparent container assembly 115. At least one positive and negative electrical wire members 124 are disposed through an interior portion of the handle assembly 186 designed to electrically couple the rod members 47A, 47B to the receiver and transmitter coil assembly 150. In this example embodiment, an optional rechargeable battery assembly 170 is disposed within the base container assembly 160 electrically coupled to at least one power port member 180. A control panel 190 is disposed in the base container assembly 160 designed to control on/off switch and the power and timing of the charge to the seated, replaceable silver wires in the top lid assembly and engage magnetic stir assembly. In this embodiment, base assembly 160 includes a raised portion 162 to secure bottom of container 110 and position inductive assembly 150 closer to impeller 142 for applying the magnetic inductive force.

In one embodiment of the colloidal brewing system, the power port member is a micro-SB port assembly 182.

In one embodiment of the colloidal brewing system, the power port member is an AC/DC power adapter assembly 184.

In one embodiment of the colloidal brewing system, a spout portion 188 is disposed on the at least one side portion opposite the handle portion 186.

In a related embodiment, the control panel 190 in the base container assembly 160 maintains on/off switch and a low voltage in the electrodes and generates a low current for enhanced colloidal silver production. In a related embodiment, a current sensor is included that is correlated to a number of parts per million of silver in the fluid, the current sensor being operatively coupled to the control panel on/off switch and with hour and minute timer 190 to also switch off power to the electrodes 47 when a predefined brew time is reached. The current sensor immersed in the fluid designed to measure current in the fluid to determine conductivity, thereby determining when the colloidal system should stop brewing.

In yet another related embodiment, system 110 has a lid member that includes an integral plug member 187 having a cap portion 187A coupled on one end to the electrical wire members designed to connect with an upper receiving plug member 187B located on the handle member 186 and coupled to the distal ends of the electrical wire members 122. In this example, cap 187A of integral plug member 187 and the upper receiving plug member 187B are coupled via separate magnetic members, the magnetic members designed to break the mechanical and electrical connection should the transparent container assembly accidentally tip over.

In yet another embodiment, a method of making a colloidal solution or brew with silver or other precious metal to have beneficial medicinal purposes is provided. The method of brewing a colloidal mineral based fluid using a colloidal generating system, similar to system 110, that includes at least a transparent container of a water-based fluid (preferably distilled water), an electrode assembly having at least two removable silver rod members coupled to two electrical wires at a distal end to form two electrodes that are spaced apart, the electrical wires adapted to be coupled at a proximal end to a power source. The method further includes the step of providing a handle member for the transparent container adapted to encase the two electrical wires to be coupled to the power source and providing a coupling plug assembly between the proximal end of the electrical wires and the handle member, wherein the coupling plug assembly includes a male and a female portion. The method further includes the step of providing a magnetic stir assembly adapted to be positioned under a closed end of the transparent container opposite the two electrodes and to provide an inductive magnetic force when powered by the power source, the magnetic stir assembly including a magnetic capsule device adapted to be place in a bottom of the transparent container and adapted to spin in response to the inductive magnetic force. An on/off switch and timer mechanism is provided to control with hours and minutes the brew time, which can be an hour or more depending on the desired level of silver particles in the fluid.

In a related embodiment, the method includes providing a control panel for an on/off switch and to control the power source which includes voltage to the electrodes and current levels in the water. The method, in a related embodiment, further includes providing a current sensor operatively coupled to the timer on the control panel and designed to measure current levels in the fluid corresponding to a conductivity of the water, such that the conductivity of the water correlates to a number of parts per million of silver particles in the fluid. The method also includes providing a lid member for the transparent container for partially encasing the electrical wires coupled to the two silver rod members.

The following patents are incorporated by reference in their entireties: U.S. Pat. and Publication Nos. 7,128,816; 2,571,688; US2011/0262556 and US2021/0237037.

While the inventive concept has been described above in terms of specific embodiments, it is to be understood that the inventive concept is not limited to these disclosed embodiments. Upon reading the teachings of this disclosure many modifications and other embodiments of the inventive concept will come to mind of those skilled in the art to which this inventive concept pertains, and which are intended to be and are covered by both this disclosure and the appended claims. It is indeed intended that the scope of the inventive concept should be determined by proper interpretation and construction of the appended claims and their legal equivalents, as understood by those of skill in the art relying upon the disclosure in this specification and the attached drawings.

The invention claimed is:

1. A colloidal brewing system comprising:
   a transparent container assembly with a watertight bottom portion and an open top portion of the container assembly, the container assembly including a handle member disposed on an outside surface of the transparent container assembly;
   a removable lid member adapted to fit on the open top portion of the container assembly and adapted to couple with a portion of the handle member, the lid member including distal ends of a positive and negative electrical wire members;
   at least two substantially silver rod members disposed on a bottom portion of the lid member with distal ends extending longitudinally downward towards the watertight bottom portion and proximal ends of the silver rod members being electrically coupled to respective distal ends of the positive and negative electrical wire members, the proximal ends of the electrical wire members extending through the handle member;
   a base container assembly adapted to receive the watertight bottom portion of the container assembly, the base container assembly adapted to support the container assembly and provide power to the electrical wire members in the handle member;
   a magnetic stir assembly substantially centering on an interior bottom portion of the container assembly and adapted to rotate on a plane parallel to the bottom portion of the container assembly upon being powered inductively by the base container; and
   a control panel disposed in the base container assembly adapted to control power and timing of the magnetic stir assembly.

2. The colloidal brewing system of claim 1 wherein the base container portion includes a rechargeable battery assembly disposed therein within the base container assembly adapted to be electrically coupled to a power port member disposed on the base container.

3. The colloidal brewing system of claim 1 wherein the power port member is an AC/DC power adapter assembly.

4. The colloidal brewing system of claim 2 wherein the at least one power port member is a micro-SB port assembly.

5. The colloidal system of claim 1 wherein a receiver coil and a transmitter coil assembly is disposed within a base container assembly and adapted to be inductively coupled to the magnetic stir assembly.

6. The colloidal system of claim 1 wherein the rod members are immersed in a water-based fluid.

7. The colloidal system of claim 1 further including a a timer mechanism for hours and minutes operatively coupled to the control panel, thereby controlling when the colloidal system should stop.

8. The colloidal system of claim 1 further including a current sensor adapted to be immersed in the fluid and further adapted to measure or determine conductivity in the fluid, thereby determining when the colloidal system should stop.

9. The colloidal system of claim 8 wherein the lid member includes an integral plug member coupled to the electrical wire members adapted to connect with an upper receiving plug member located on the handle member and coupled to the distal ends of the electrical wire members.

10. The colloidal system of claim 9 wherein the integral plug member and the upper receiving plug member are coupled via separate magnetic members, the magnetic members adapted to break the connection should the transparent container assembly accidentally tip over.

11. The colloidal brewing system of claim 1 wherein the control panel in the base container assembly maintains a low voltage in the electrodes and generates a low current for enhanced colloidal silver production.

12. The brewing system of claim 8 wherein the current sensor is correlated to a number of parts per million of silver in the fluid, the current sensor being operatively coupled to the control panel to switch off power to the electrodes when a predefined silver threshold is reached.

13. The brewing system of claim 1 wherein the magnetic stir assembly is adapted to reduce silver particle clumping in a fluid in the transparent container assembly.

14. The brewing system of 1 wherein the magnetic stir assembly includes an impeller positioned on a stem or rod adapted to spin upon receiving an inductive magnetic force adjacent to the impeller.

15. A method of brewing a colloidal mineral based fluid using a colloidal generating system, the colloidal generating system including at least a transparent container of a water-based fluid, an electrode assembly having at least two replaceable silver rod members coupled to two electrical wires at a distal end to form two electrodes that are spaced apart, the electrical wires adapted to be coupled at a proximal end to a power source, the method comprising the steps of:
   providing a handle member for the transparent container adapted to encase the two electrical wires to be coupled to the power source;
   providing a coupling plug assembly between the proximal end of the electrical wires and the handle member, wherein the coupling plug assembly includes a male and a female portion; and
   providing a magnetic stir assembly adapted to be positioned under a closed end of the transparent container opposite the two electrodes and to provide an inductive magnetic force when powered by the power source, the magnetic stir assembly including a magnetic capsule device adapted to be place in a bottom of the transparent container and adapted to spin in response to the inductive magnetic force.

16. The method of claim 15 wherein each of the male and female portions of the coupling plug includes a magnetic member to facilitate the electrical connection and to facilitate quickly breaking the electrical connection where the transparent container is accidentally tipped over.

17. The method of claim 15 further providing a control panel to control the power source which includes controlling both voltage to the electrodes and current levels in distilled water.

18. The method of claim 17 further providing a current sensor operatively coupled to the control panel and adapted to measure current levels in the fluid corresponding to a conductivity of the water.

19. The method of claim 18 wherein the conductivity of the water correlates to a number of parts per million of silver particles in the fluid or the control panel hours and minutes for brew time.

20. The method of claim 15 further including the step of providing a lid member for the transparent container for partially encasing the electrical wires coupled to the two replaceable silver rod members.

\* \* \* \* \*